US010082657B2

(12) United States Patent
Hamilton et al.

(10) Patent No.: US 10,082,657 B2
(45) Date of Patent: Sep. 25, 2018

(54) DUAL MAGNIFICATION APPARATUS AND SYSTEM FOR EXAMINING A SINGLE OBJECTIVE IN A SCANNING OPTICAL MICROSCOPE USING TWO WAVELENGTHS OF LIGHT

(71) Applicant: The United States of America as represented by the Secretary of the Navy, Washington, DC (US)

(72) Inventors: Brett J Hamilton, Heltonville, IN (US); David S Stoker, Belmont, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/623,848

(22) Filed: Jun. 15, 2017

(65) Prior Publication Data
US 2018/0052313 A1 Feb. 22, 2018

Related U.S. Application Data

(60) Provisional application No. 62/375,994, filed on Aug. 17, 2016, provisional application No. 62/488,367, filed on Apr. 21, 2017.

(51) Int. Cl.
*G01N 21/00* (2006.01)
*G02B 21/02* (2006.01)
(Continued)

(52) U.S. Cl.
CPC ............ *G02B 21/02* (2013.01); *G01N 1/44* (2013.01); *G01N 21/6458* (2013.01); *G01N 21/9501* (2013.01); *G01N 33/4833* (2013.01); *G02B 21/008* (2013.01); *G02B 21/0032* (2013.01); *G02B 21/0048* (2013.01); *G02B 21/0064* (2013.01); *G02B 21/18* (2013.01); *G02B 21/30* (2013.01); *G01N 2201/06113* (2013.01)

(58) Field of Classification Search
CPC .......... G01N 21/6458; G01N 21/6428; G01N 2500/10; G01N 33/53; G01N 33/582; G01N 2021/6439; G01N 21/645; G01N 21/6452; G01N 33/5014; G01N 2021/6421; G01N 2021/6478; G01N 33/57484; G01N 2021/6417
See application file for complete search history.

(56) References Cited

U.S. PATENT DOCUMENTS 3,459,464 A * 8/1969 Smith .................... G02B 15/00
359/376
3,877,779 A * 4/1975 Pierse .................... G02B 21/20
359/374
(Continued)

*Primary Examiner* — Michael P Stafira
(74) *Attorney, Agent, or Firm* — Christopher A. Monsey

(57) ABSTRACT

Dual magnification systems and apparatuses for testing and viewing a single objective in a scanning optical microscope and methods of using the systems and apparatuses are provided. Two optical paths allow two wavelengths of light to be magnified to separate magnification levels such that a lower magnification optical path can be used to examine a target area while a higher magnification optical path can be used to examine a subset of the target area and elicit test sample responses to localize a condition of interest.

12 Claims, 7 Drawing Sheets

(51) Int. Cl.
*G02B 21/00* (2006.01)
*G02B 21/30* (2006.01)
*G01N 1/44* (2006.01)
*G01N 21/95* (2006.01)
*G01N 21/64* (2006.01)
*G01N 33/483* (2006.01)
*G02B 21/18* (2006.01)

(56) References Cited

U.S. PATENT DOCUMENTS

| | | | |
|---|---|---|---|
| 4,641,931 A * | 2/1987 | Loy | G02B 23/12 |
| | | | 250/214 VT |
| 4,863,253 A | 9/1989 | Shafer et al. | |
| 5,034,613 A * | 7/1991 | Denk | G01N 21/6402 |
| | | | 250/458.1 |
| 6,459,490 B1 | 10/2002 | Kuhn et al. | |
| 7,307,801 B1 | 12/2007 | Lundgren | |
| 7,532,417 B2 | 5/2009 | Lundgren | |
| 8,294,808 B2 | 10/2012 | Caron | |
| 2007/0183029 A1* | 8/2007 | Iketaki | G02B 21/0032 |
| | | | 359/385 |
| 2013/0015370 A1* | 1/2013 | Damaskinos | G01N 21/6452 |
| | | | 250/459.1 |
| 2015/0304552 A1* | 10/2015 | Matsuzaki | G02B 21/18 |
| | | | 348/80 |
| 2016/0123813 A1* | 5/2016 | Kyogaku | G01N 21/65 |
| | | | 356/301 |

* cited by examiner

Step 201: Placing a testing sample in a sample chamber

Step 203: Directing a first laser having a first wavelength of light through a first optical path to output the first laser from the dual magnification apparatus at a first magnification level Step 205: Directing the first laser at the first magnification level onto a first target area of the testing sample Step 207: Recording a first plurality of images resulting from the first laser reflecting off of the first target area with a first wavelength detector Step 209: Directing a second laser having a second wavelength of light through a second optical path to output the second laser from the dual magnification apparatus at a second magnification level Step 211: Directing the second laser at the second magnification level onto a second target area on the testing sample to elicit testing sample responses Step 213: Recording a second plurality of images resulting from the second laser activating a sample response and reflecting off of the second target area with a second wavelength detector Step 215: Localizing the location of at least one condition of interest by adjusting or scanning the second target area while monitoring the first and second pluralities of images until at least one local maximum of testing sample responses is found

Fig. 6

Step 231: Providing a dual magnification system comprising a first and second laser generator, a dual magnification apparatus, a sample chamber, an external stimulation device, a first and second wavelength detector, a control computer, and a graphical display Step 233: Placing a testing sample in a sample chamber Step 235: Directing a first laser having a first wavelength of light through a first optical path to output the first laser from the dual magnification apparatus at a first magnification level Step 237: Directing the first laser at the first magnification level onto a first target area of the testing sample Step 239: Applying an electrical stimulus to the testing sample with an external stimulation device Step 241: Recording a first plurality of images of signal activity resulting from the first laser reflecting off of the first target area with the first wavelength detector Step 243: Directing a second laser having a second wavelength of light through a second optical path to output the second laser from the dual magnification apparatus at a second magnification level Step 245: Directing the second laser at the second magnification level onto a second target area on the testing sample to activate at least one fault condition within the testing sample Step 247: Recording a second plurality of images of signal activity resulting from the second laser activating at least one fault condition and reflecting off of the second target area with a second wavelength detector Step 249: Localizing the location of the at least one fault condition by adjusting or scanning the second target area while monitoring the first and second pluralities of images until at least one local maximum of signal activity disruptions is found

Fig. 7

DUAL MAGNIFICATION APPARATUS AND SYSTEM FOR EXAMINING A SINGLE OBJECTIVE IN A SCANNING OPTICAL MICROSCOPE USING TWO WAVELENGTHS OF LIGHT

CROSS-REFERENCE TO RELATED APPLICATIONS

The present application claims priority to U.S. Provisional Patent Application Ser. No. 62/375,994, filed Aug. 17, 2016, entitled "DUAL MAGNIFICATION APPARATUS FOR A SINGLE OBJECTIVE IN A SCANNING OPTICAL MICROSCOPE," and priority to the U.S. Provisional Patent Application Ser. No. 62/488,367, filed Apr. 21, 2017, entitled "DUAL MAGNIFICATION APPARATUS AND SYSTEM FOR EXAMINING A SINGLE OBJECTIVE IN A SCANNING OPTICAL MICROSCOPE USING TWO WAVELENGTHS OF LIGHT", the disclosures of which are expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (Navy Case 200,428) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

The present invention relates to improvements in optical microscopes permitting a view within a view such as with a pump-probe microscopy system.

Current state-of-the-art limits the operator of scanning optical microscopes in a variety of ways such as limiting operators to single magnification objectives. This means a compromise must be made between resolution (hi mag) and size of field of view (low mag). This greatly limits the usage of pump-probe methods for use in a variety of areas. For example, a cause-effect analysis is important for non-destructive failure analysis of integrated circuits as well as for a variety of other applications including in medical fields. Existing designs do not teach how to independently adjust magnification for each field of the fields of view. Existing systems related to stereo imaging do not teach how to independently adjust magnification for each image in stereo pair and are otherwise limited to low (10×) magnification.

Existing systems use dual magnification imaging systems, but they are insufficient to provide the necessary functionality to achieve a simultaneous coordination between low and high-mag laser confocal imaging. In U.S. Pat. No. 8,294,808, a single optical element is used to demonstrate a dual focus imaging system, however the methods do not provide a solution for achieving overlapping imaging planes, nor do the methods specify a high magnification objective system with a flat imaging field. In U.S. Pat. Nos. 7,532,417 and 7,307,801, different magnifications are achieved by mechanically repositioning optical surfaces, but simultaneous, different magnifications are not realizable with the system. In U.S. Pat. No. 6,459,490 methods are claimed for a dual image formation system, not a dual microscope objective. Finally, U.S. Pat. No. 4,863,253 provides a means of creating different magnifications with a single, high-magnification objective, however the focal planes for each magnification are not overlapped in space, and the objective is not compatible with infinity-corrected, laser confocal imaging systems.

To take full advantage of new pump probe microscope techniques, methods and systems are needed to disrupt or elicit a response from a system or sample (e.g., an integrated circuit) with precision using high magnification optics while simultaneously observing the effect throughout the entire system using low magnification optics (e.g., changing a functioning integrated circuit at high magnification while observing changes to the circuit function at locations beyond the pump focus). Currently existing systems are unable to provide these functions and subsequent benefits.

In some exemplary embodiments of the invention, a dual magnification apparatus allows two levels of magnification simultaneously. A high magnification region allows enhanced resolution for system stimulation, as well as precise manipulation of the field of view, while a low magnification region allows a much larger field of view for observing the stimulation response among other purposes. A variety of structures and methods are provided which provide a variety of needed improvements.

In an exemplary method, a user can place a testing sample in an exemplary system and use recorded responses to shift the target areas of two laser sources to observe responses and localize a desired test sample or object of interest (e.g., a particular type of biological cell, an integrated circuit defect). In exemplary methods, lasers of differing wavelengths can be chosen such that one laser can elicit test sample responses and the other laser can provide view of the test sample responses.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 6 shows an exemplary method of using a dual-magnification system to test a sample.

FIG. 7 shows an exemplary method of using a dual-magnification system to test an integrated circuit for fault conditions.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Features of exemplary embodiments of a dual field of view (FOV) system can include a dual magnification microscope lens system. Some embodiments can include systems where magnifications are wavelength dependent—different optics are traversed based on wavelength, have simultaneous data collection at different fields of view, and have working distance that are non-contact, and can be used for non-immersion lens applications. In at least some embodiments, a system can include at least two adjustable optical elements (AOE), with a minimum one per wavelength. Embodiments can include a tip or tilt capability that can be used to manipulate a center of field of view. Systems can enable capabilities or structures for spacing adjusted to manipulate working distance. Embodiments can provide capabilities that do not require computational reconstruction and can be compatible with standard microscope turret (fluorescence imaging and confocal laser scanning). Magnification optics can be designed to compensate for aberrations created by the splitter and combiner pairs.

Embodiments of the invention can provide ability to simultaneously record data from different locations/depths at high magnification. For example, when observing simultaneous activity from widely separated neurons in a 3D tissue. Embodiments can provide a capability for observing photoemissions from an entire integrated circuit while locally altering the function of a single transistor. Other capabilities provided can include an ability to orient and target high magnification areas while simultaneously observing large scale behavior. For example, when performing laser ablation of sub-cellular structures. In exemplary embodiments, a wavelength for at least one laser can be selected to elicit a response with a test sample (e.g., a 1064 nm laser to trigger fault conditions in an integrated circuit).

Figure 1:
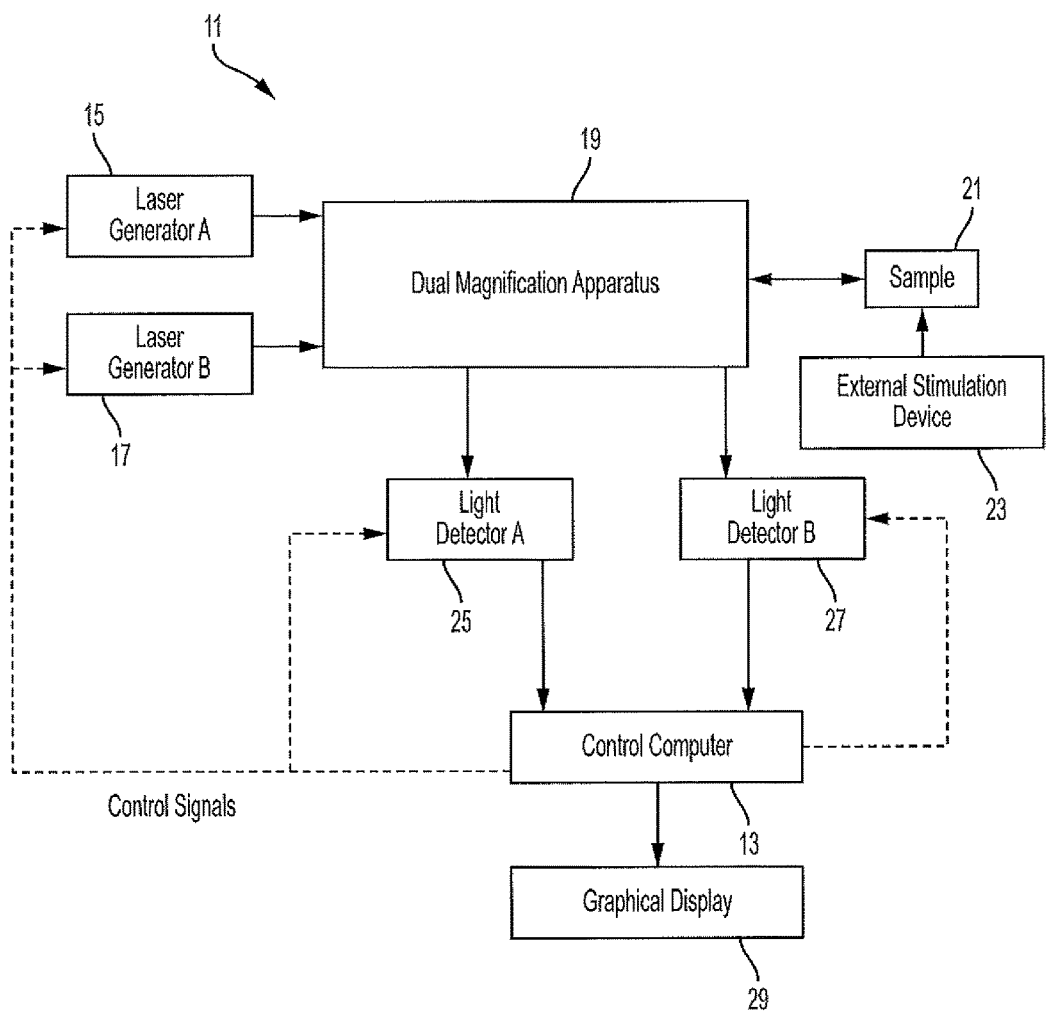
FIG. 1 shows a block diagram of an exemplary dual-magnification system for testing samples using two wavelengths of light.

FIG. 1 shows a block diagram of an exemplary dual-magnification system 11 for testing a test sample 21 using two wavelengths of light. A control computer 13 can send control signals to a first laser generator 15 and a second laser generator 17 with instructions to output light at a first and second wavelength (e.g. 1300 nm and 1050 nm), respectively. A control computer 13 can also send control signals to a first light detector and a second light detector configured to detect light having the first and second wavelength, respectively. The first laser generator 15 and second laser generator 17 can output light on a first and second optical path, respectively, each of which passes through a dual magnification apparatus 19. Within the dual magnification apparatus 19, the two lasers can be split by a first optical element (e.g. a refractive lens that is transmissive to the first wavelength and reflective to the second wavelength) such that the first optical path can travel through a series of optical doublets to magnify the first wavelength of light at a first magnification, and the second optical path can travel through a series of optical doublets to magnify the second wavelength of light at a second magnification. After magnification, the dual magnification apparatus 19 can combine the two optical paths with a second optical element (e.g. a refractive lens that is reflective to the first wavelength and transmissive to the second wavelength) such that both wavelengths of light are directed towards the same relative region of a test sample 21. Light reflecting off of a test sample 21 can then re-enter the dual magnification apparatus 19 along the first and second optical paths such that the first and second wavelengths can be separated by the first and second optical elements to redirect the first and second wavelengths towards the first light detector 25 and second light detector 27, respectively. An external stimulation device 23 (e.g., an electrical current generator) can be connected to a test sample 21 to elicit a response from or stimulate the test sample 21 (e.g. pass a current through an integrated circuit, heat a cell culture). An external stimulation device can activate a condition within a test sample (e.g., powering an integrated circuit) such that the test sample will show a response once a probing laser strikes the test sample (e.g., causing a fault in a powered integrated circuit). An external stimulation device 23 can be controlled by the control computer 13 (e.g., preprogrammed electrical stimulation) or independently controlled. The first light detector 25 and second light detector 27 can generate a plurality of signals upon detecting corresponding wavelengths of light and send the plurality of detection signals to the control computer 13. The control computer 13 can then process the plurality of detection signals into a plurality of image signals and send the plurality of image signals to a graphical display 29 (e.g. a computer monitor). A graphical display 29 can be programmed in a variety of ways to show resulting images of the first and second optical paths simultaneously in a variety of formats and configurations (e.g., side by side image display, one image embedded within another, color spectrum images displaying relative brightness of test sample responses within a target area). A graphical display 29 can show images in real time such that test sample responses can be immediately recognized so that an operator of the system can make adjustments to increase or decrease test sample responses. In an alternative exemplary embodiment, a multispectral light source (e.g., a white light) can create multiple wavelengths of light such that a first and second wavelength of light can originate from the same multispectral light source.

Figure 2:
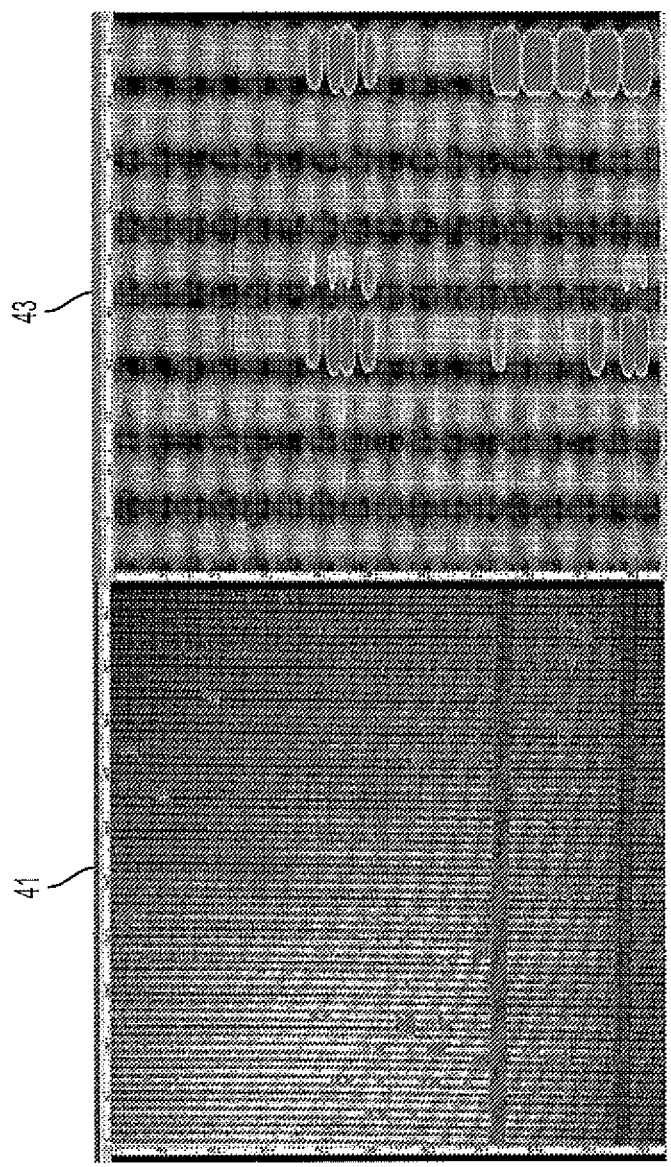
FIG. 2 shows an exemplary graphical display for viewing low and high magnification images captured by a dual-magnification system.
Figure 3:
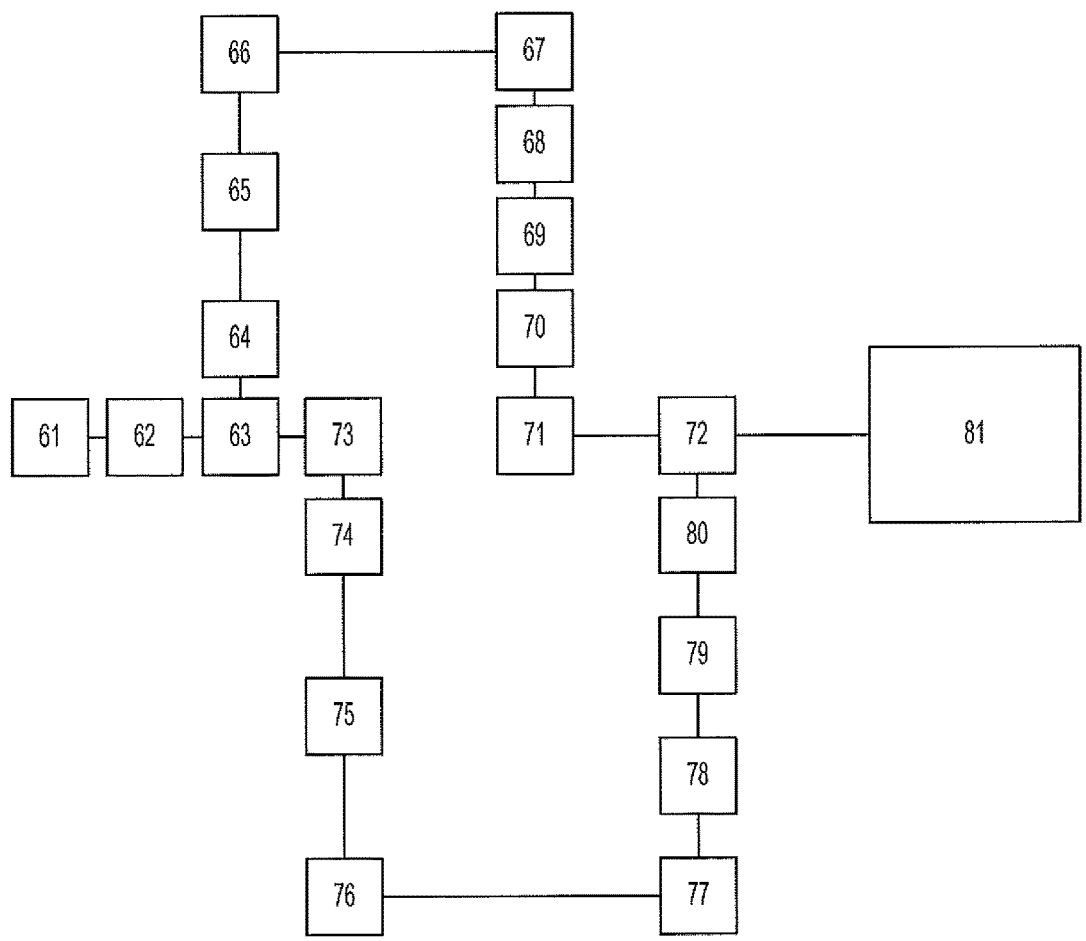
FIG. 3 shows an exemplary block diagram of a dual-magnification apparatus.

FIG. 2 shows an exemplary graphical display showing images generated from an exemplary dual magnification system (e.g., as shown in FIG. 1). A low magnification view 41 and a high magnification view 43 can be shown simultaneously, wherein the low magnification image can show a first target area and the high magnification image can show a second target area which is a subset of the first target area. In the low magnification image 41 and high magnification image 43, conditions of interest resulting from the first and wavelengths of light interacting can be shown FIG. 3 shows a simplified diagram of various elements of one embodiment of this disclosure. A first subset of optical elements is provided which are disposed and form a first optical path for a first wavelength of light having an optical wavelength of lambda B. A second subset of optical elements are provided which are disposed and form a second optical path for a second wavelength of light having an optical wavelengths lambda A. The first optical path comprises a first path that passes through the first subset of optical elements comprising optical elements 61, 62, 63, 64, 65, 66, 67, 68, 69, 70, 71, 72, and 21. The second optical path comprises a second path that passes through the second subset of optical elements comprising optical elements 61, 62, 63, 73, 74, 75, 76, 77, 78, 79, 72, and 21. A first optical doublet 61 is provided. In at least some embodiments, optical doublets are two lenses having different indices of refraction. In at least some embodiments, the two lenses of an optical doublet can be optically cemented or formed together. A second optical doublet 62 is provided. A first dichroic optical assembly 63 (e.g., an element that reflects the first wavelength of light having optical wavelength Lambda B and transmits or passes through the second wavelength of light having optical wavelength Lambda A) is provided. In some embodiments, the first dichroic optical assembly 63 can be an element that reflects wavelength lambda B ninety degrees and transmits wavelength lambda A without attenuation or changing its direction. A third and fourth optical doublet 64, 65 are provided. An adjustable first reflecting element 66 is provided which can independently adjust a center of a field of view for the first wavelength of light. A fixed second reflecting element 67 is provided. Fifth, sixth, and seventh optical doublets are provided in 68, 69, and 70. A fixed third reflecting element 71 is also provided to receive the first wavelength of light. A second dichroic optical assembly 72 comprising a dichroic element and a lens is provided that includes a dichroic surface that transmits Lambda B and reflects Lambda A as well as an optical lens that is placed in the Lambda A path but not in the Lambda B path. An exemplary second dichroic optical assembly 72 comprises a first portion that includes a ninety degree reflector at wavelength lambda A, second portion that is transmissive to wavelength lambda B, and a third portion including a surface traversed only by wavelength lambda A that is of a refractive, spherical shape. A fourth reflecting element 73 is also provided. An eighth and ninth optical doublet 74, 75 are provided. An adjustable fifth reflecting element 76 is provided. A fixed sixth reflecting element 77 is provided. A tenth, eleventh, and twelfth optical doublet 78, 79, and 80 are provided. The tenth optical doublet 78 can be disposed on the second optical path at a position so that its optical axis can be adjusted to change a focal plane of the second optical path. The first, second, third, fourth, fifth, and sixth reflecting elements (66, 67, 71, 73, 76, 77) can be configured to reflect light at approximately ninety degree angles. In at least some alternative embodiments, each of optical doublets 61, 62, 64, 65, 68, 69, 70, 74, 75, 78, 79, 80 can be replaced by equivalent structures such as a plurality of separated optical or aspherical lenses with nonzero conical constants which can be air spaced, cemented, or oiled. In at least some alternative embodiments, each of reflecting elements 66, 67, 71, 73, 76, 77 can be replaced by equivalent structures such as metallized surfaces or right angled prisms that cause light to undergo total internal reflection.

Embodiments of the invention, e.g., as shown in FIG. 3, place a first optical surface of the first optical doublet 61 at a pupil plane of an imaging system. In this manner, an embodiment can accept light from two independently scanned laser beams, possibly from two separate galvo laser scan units located in a confocal laser scanning microscope, or possibly a light emitting diode (LED) light source or high fidelity IR laser light source, and can create two fields of view whose focal planes coincide, but the magnifications of those two focal planes are different. One magnification is large enough to observe a global perspective of a sample under investigation; the other is much higher and used to observe details. In some embodiments, the exact field of view of the high magnification microscope can be adjustable along the x, y, and z planes, while the low magnification view can be fixed. Splitting wavelengths of light into two optical paths can allow changes to be made independently to the two fields of view.

In at least some embodiments, an optical system generates a bundle of light rays (e.g. by a first and second light generator, by a multispectral light source) from different angles that overlap at the entrance pupil of the first optical doublet 61. The first dichroic optical assembly 63 can be dichroic, and separates the first and second optical paths based on respective wavelengths of light. All wavelengths can be recombined with the second dichroic optical assembly 72 such that all optical wavelengths interact with the same test sample 21. Each subset of optical elements may be traversed in both directions, such that light may travel from optical doublet 61 toward the test sample 21, and light may also travel from the test sample 21, toward the first optical doublet 61.

In the first optical path, including elements 64, 65, 66, 67, 68, 69, 70, and 71, a first dichroic optical assembly 63 relays a first wavelength of light onto a first pupil of the third optical doublet, wherein the first pupil intersects the reflective surface of the first reflecting element 66 before then traversing a plurality of lenses contained in elements 67-71 to create a specific lower (of the two optical paths) numerical aperture and, therefore, lower magnification. Because the first reflecting element 66 coincides with the images pupil plane of the first subset of optical elements, it allows a user to manipulate x, y locations of a low magnification field of view which contains any number of higher magnification fields of view.

In the second optical path (elements 73, 74, 75, 76, 77, 78, 79, and 80), a first dichroic optical assembly 63 relays a second wavelength of light onto a second pupil of the eighth optical doublet, wherein the second pupil intersects the reflecting surface of the fifth reflecting element 76 before then traversing a plurality of lenses contained in elements 76-80. The fifth reflecting element 76 may be angle-adjusted without displacement in order to manipulate the transverse position of a higher magnification field of view that is nested within the lower magnification field of view created by the first optical path. The higher magnification is created by the plurality of lenses contained in Elements 78, 79, 80, and 72, which additionally creates a focal plane in the test sample 21 that is nested within the focal volume created by the elements in the first optical path. Moreover, the tenth optical doublet 78 may be displaced in order to reposition the focal plane of the second optical path within the focal volume of the first optical path. The second dichroic optical assembly 72 can be both dichroic and refractive such that it simultaneously combines the optical paths and adjusts the focusing properties of the second optical path.

Together the optical elements and their relationship allow for the first field of view to be nested within the second larger field of view and the center of the nested field of view to be repositioned within the larger field of view.

Figure 4:
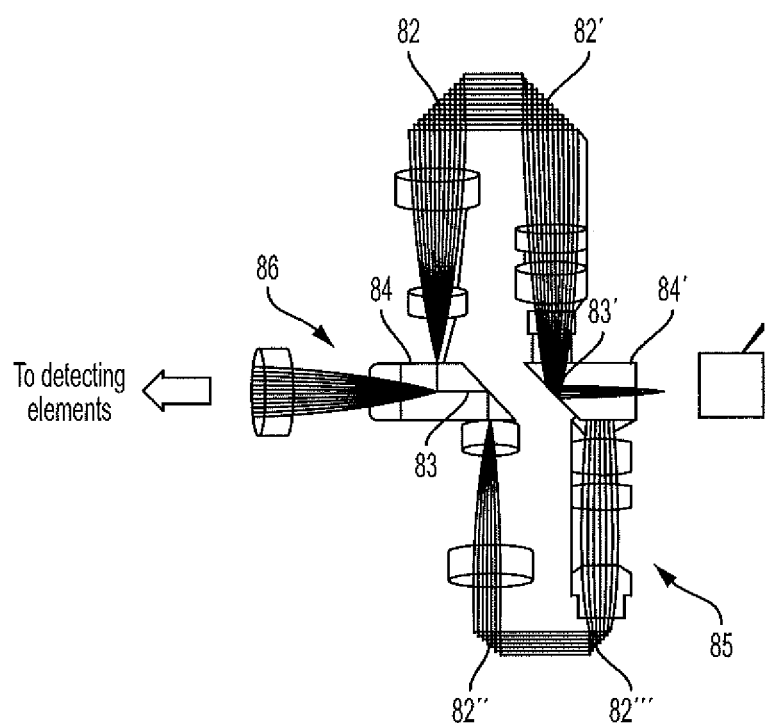
FIG. 4 shows an exemplary dual-magnification apparatus.

FIG. 4 shows an exemplary embodiment of the invention wherein curvature, placement and material properties of all optical elements have been defined. This embodiment can include mirrors 82, 82', 82", and 82'", which are components of the first, second, fifth, and sixth reflecting elements (not shown), respectively, that can be used to reflect an image through a series of lenses. Right angled prisms 83, 83', which are components of the third and fourth reflecting elements (not shown), respectively, can rotate light paths by ninety degrees and may be optically cemented to dichroic optics 84, 84', which are components of the first and second dichroic optical assemblies (not shown) and may include optically cemented right angle prisms whose contact point contains a dichroic optical coating. A computer operated, gear-driven or piston-driven stage 85 can be used to change the focal plane of one optical path. A standard mechanical screw thread 86 can allow the optical system to be mounted onto commercial microscope turrets. An exemplary detailed set of optical surfaces traversed by first and second wavelengths of light respectively having wavelengths lambda B and lambda A is contained in Tables 1 and 2. This specific embodiment includes a variant that can be used to define a lower magnification (Numerical Aperture, NA=0.07) field of view for a set of wavelengths between 1300 and 1600 nm, as well as a higher magnification field of view (NA=0.25) for a narrow range of wavelength near 1050 nm.

TABLE 1

Upper optical surfaces traversed by lambda B = (1300-1600 nm)

| Surf | Type | Radius | Thickness | Glass | Diameter | Conic |
|---|---|---|---|---|---|---|
| OBJ | STANDARD | Infinity | Infinity | | 0 | 0 |
| STO | STANDARD | Infinity | 0 | | 16 | 0 |
| 2 | STANDARD | 16.66203 | 4 | CAF2 | 16 | 0 |
| 3 | STANDARD | −17.2108 | 4 | F2 | 16 | 0 |
| 4 | STANDARD | −49.8825 | 13 | | 16 | 0 |
| 5 | STANDARD | 12.08521 | 4 | CAF2 | 10 | 0 |
| 6 | STANDARD | −9.28829 | 2.000001 | BAFN6 | 10 | 0 |
| 7 | STANDARD | −29.7421 | 0.987247 | | 10 | 0 |
| 8 | STANDARD | Infinity | 5 | BK7 | 10 | 0 |
| 9 | TILTSURF | — | 0 | MIRROR | 2.933446 | — |
| 10 | COORDBRK | — | 0 | | — | — |
| 11 | TILTSURF | — | −5 | BK7 | 2.933446 | — |
| 12 | STANDARD | Infinity | −7.74437 | | 1.883818 | 0 |
| 13 | STANDARD | −29.742 | −2 | BAFN6 | 10 | 0 |
| 14 | STANDARD | −9.288 | −4 | CAF2 | 10 | 0 |
| 15 | STANDARD | 12.085 | −13 | | 10 | 0 |
| 16 | STANDARD | −49.882 | −4 | F2 | 16 | 0 |
| 17 | STANDARD | −17.211 | −4 | CAF2 | 16 | 0 |
| 18 | STANDARD | 16.662 | −10.6067 | | 16 | 0 |
| 19 | TILTSURF | — | 0 | MIRROR | 9.997514 | — |
| 20 | COORDBRK | — | 0 | | — | — |
| 21 | TILTSURF | — | 20 | | 9.997514 | — |
| 22 | TILTSURF | — | 0 | MIRROR | 12.18342 | — |
| 23 | COORDBRK | — | 0 | | — | — |
| 24 | TILTSURF | — | −20.7888 | | 12.18342 | — |
| 25 | STANDARD | −20.8181 | −2.85801 | SRF2 | 13.49535 | 0 |
| 26 | STANDARD | −49.4124 | −2.01876 | N-BAF51 | 13.17459 | 0 |
| 27 | STANDARD | −122.109 | −1.04629 | | 12.89071 | 0 |
| 28 | STANDARD | −10.7005 | −2.84416 | PYREX | 12.32914 | 0 |
| 29 | STANDARD | 20.15268 | −4.78456 | LF5 | 12.37536 | 0 |
| 30 | STANDARD | −97.5946 | −2.16275 | | 9.64292 | 0 |
| 31 | STANDARD | 38.9137 | −4.7976 | C06-44 | 8.395092 | 0 |
| 32 | STANDARD | 6.503714 | −2.99481 | N-K5 | 7.08451 | 0 |
| 33 | STANDARD | −4.22975 | −1.10426 | | 5.000008 | 0 |
| 34 | STANDARD | Infinity | −5 | BK7 | 5.018025 | 0 |
| 35 | TILTSURF | — | 0 | MIRROR | 5.34415 | — |
| 36 | COORDBRK | — | 0 | | — | — |
| 37 | TILTSURF | — | 5 | BK7 | 5.34415 | — |
| 38 | STANDARD | Infinity | 0 | | 5.443685 | 0 |
| 39 | STANDARD | Infinity | 10 | BK7 | 5.443685 | 0 |
| 40 | STANDARD | Infinity | 5 | | 5.871252 | 0 |
| IMA | STANDARD | Infinity | | | 10 | 0 |

TABLE 2

Lower optical surfaces traversed by lambda A = 1050 nm

| Surf | Type | Radius | Thickness | Glass | Diameter | Conic |
|---|---|---|---|---|---|---|
| OBJ | STANDARD | Infinity | Infinity | | 0 | 0 |
| STO | STANDARD | Infinity | 0 | | 16 | 0 |
| 2 | STANDARD | 16.66203 | 4 | CAF2 | 16 | 0 |
| 3 | STANDARD | −17.2108 | 4 | F2 | 16 | 0 |
| 4 | STANDARD | −49.8825 | 13 | | 16 | 0 |
| 5 | STANDARD | 12.08521 | 4 | CAF2 | 10 | 0 |
| 6 | STANDARD | −9.28829 | 2.000001 | BAFN6 | 10 | 0 |
| 7 | STANDARD | −29.7421 | 0.987247 | | 10 | 0 |
| 8 | STANDARD | Infinity | 10 | BK7 | 10 | 0 |
| 9 | STANDARD | Infinity | 5 | BK7 | 10 | 0 |
| 10 | TILTSURF | — | 0 | MIRROR | 2.396967 | — |
| 11 | COORDBRK | — | 0 | | — | — |
| 12 | TILTSURF | — | −5 | BK7 | 2.396967 | — |
| 13 | STANDARD | Infinity | −0.25072 | | 3.251546 | 0 |
| 14 | STANDARD | −29.742 | −2 | BAFN6 | 10 | 0 |
| 15 | STANDARD | −9.288 | −4 | CAF2 | 10 | 0 |
| 16 | STANDARD | 12.085 | −15.647 | | 10 | 0 |
| 17 | STANDARD | −49.882 | −4 | F2 | 16 | 0 |
| 18 | STANDARD | −17.211 | −4 | CAF2 | 16 | 0 |
| 19 | STANDARD | 16.662 | −9.40245 | | 16 | 0 |
| 20 | TILTSURF | — | 0 | MIRROR | 4.5 | — |
| 21 | COORDBRK | — | 0 | | — | — |
| 22 | TILTSURF | — | 10 | | 4.441978 | — |

TABLE 2-continued

Lower optical surfaces traversed by lambda A = 1050 nm

| Surf | Type | Radius | Thickness | Glass | Diameter | Conic |
|---|---|---|---|---|---|---|
| 23 | STANDARD | Infinity | 10 | | 5.070528 | 0 |
| 24 | TILTSURF | — | 0 | MIRROR | 5.650263 | — |
| 25 | COORDBRK | — | −5 | | — | — |
| 26 | STANDARD | 5.664983 | −5.81924 | N-SK5 | 6.207719 | 0 |
| 27 | STANDARD | 4.581814 | −3.324 | F2HT | 8.292307 | 0 |
| 28 | STANDARD | 8.879719 | −9.32052 | | 10.5884 | 0 |
| 29 | STANDARD | −160.012 | −2.10118 | N-SF14 | 10.96387 | 0 |
| 30 | STANDARD | −10.3263 | −2.52371 | LITHOSIL-Q | 10.9296 | 0 |
| 31 | STANDARD | 20.55969 | −1.58691 | | 10.98124 | 0 |
| 32 | STANDARD | −43.2086 | −2.36081 | N-SK11 | 11.26724 | 0 |
| 33 | STANDARD | −27.9476 | −3.66914 | BAF52 | 11.2013 | 0 |
| 34 | STANDARD | −1610.81 | −1.55471 | | 11.09022 | 0 |
| 35 | STANDARD | −9.72999 | −2.13977 | N-SK16 | 10.92004 | 0 |
| 36 | STANDARD | Infinity | 0 | | 10.67954 | 0 |
| 37 | STANDARD | Infinity | −5 | BK7 | 10.67954 | 0 |
| 38 | TILTSURF | — | 0 | MIRROR | 10.94151 | — |
| 39 | COORDBRK | — | 0 | | — | — |
| 40 | TILTSURF | — | 5 | BK7 | 10.94151 | — |
| 41 | STANDARD | Infinity | 5 | | 5.114688 | 0 |
| IMA | STANDARD | Infinity | | | 10 | 0 |

With regard to embodiments with a laser objective scanning microscope, a location where changes are accomplished can have significance. For example, in an embodiment similar to, e.g., FIG. 3 or 4, a bottom lens assembly may have no need to reposition the FOV for an overall area however top lens assembly elements are significant as where light is split off at the top, an angle could be adjusted in a way that it does not alter the focal plane or change the size of the field of view. To do that, a turning mirror can be used, e.g., two flat mirrors where one of them needs to rotate to move the field of view within the first FOV. A relay system can take light from dichroic beam splitter, splits it, then images the resulting image onto a second turning mirror, then the second turning mirror will rotate so the second turning mirror can then manipulate the field of view without altering the focal plane.

Figure 5:
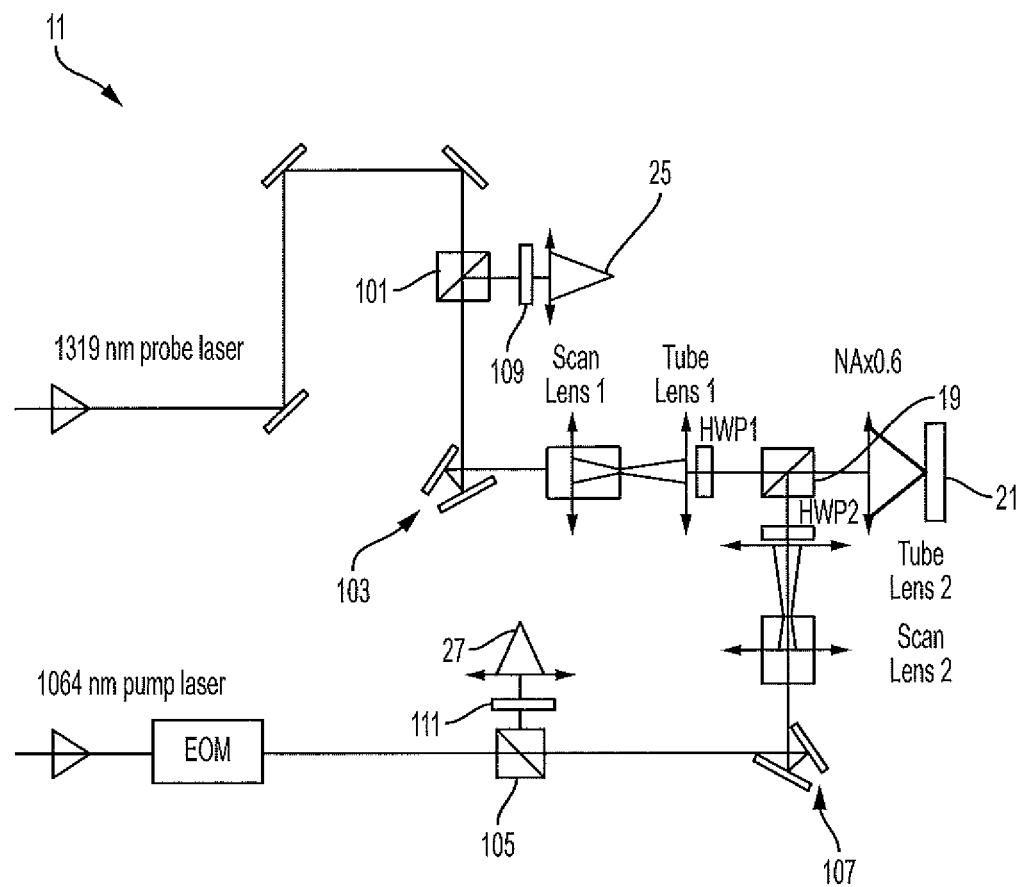
FIG. 5 shows an exemplary dual-magnification system.

FIG. 5 shows an exemplary dual-magnification system 11 similar to that shown in FIG. 1 utilizing two lasers with different wavelengths of light. A first laser generator and second laser generator can output light on a first and second optical path, respectively. Light from the first laser generator can pass through a first beam splitter 101 which is transmissive to light originating from the first laser generator and reflective to light originating from reflections of a test sample 21. A first galvo 103 can make alterations to the first optical path to alter a first target area of the first wavelength of light. Likewise, light from the second laser generator can pass through a second beam splitter 105 which is transmissive to light originating from the second laser generator and reflective to light originating from test sample 21 reflections. A second galvo 107 can make alterations to the second optical path to alter a second target area of the second wavelength of light. Both optical paths enter the dual-magnification apparatus 19. Light reflecting off of the test sample 21 can return through the first and second optical paths until reaching the optical element 101 can then be directed into a first light detector 25. A first wavelength filter 109 can be placed between optical element 101 and a first light detector 25 to prevent foreign light sources from entering the first light detector 25. Light reflected off of the optical element 105 can then be directed into a second light detector 27. A second wavelength filter 111 can be placed between optical element 105 and a second light detector 27 to prevent foreign light sources from entering the second light detector 27.

FIG. 6 shows an exemplary method of using a dual-magnification system to stimulate a test sample and record responses to the stimulation. At step 201 placing a test sample in a sample chamber. At step 203 directing a first laser having a first wavelength of light through a first optical path to output the first laser from the dual magnification apparatus at a first magnification level. At step 205 directing the first laser at the first magnification level onto a first target area of the test sample. At step 207, recording a first plurality of images of signal activity resulting from the first laser reflecting off of the first target area with a first wavelength detector. Step 209, directing a second laser having a second wavelength of light through a second optical path to output the second laser from the dual magnification apparatus at a second magnification level. At step 211 directing the second laser at the second magnification level onto a second target area on the test sample to elicit test sample responses. At step 213 recording a second plurality of images resulting from the second laser activating a sample response and reflecting off of the second target area with a second wavelength detector. At step 215 localizing the location of at least one condition of interest by adjusting the second target area while monitoring the first and second pluralities of images until at least one local maximum of test sample responses is found.

FIG. 7 shows an exemplary method of using a dual-magnification system to test an integrated circuit for fault conditions. At step 231 providing a dual magnification system comprising a first and second laser generator, a dual magnification apparatus, a sample chamber, an external stimulation device, a first and second wavelength detector, a control computer, and a graphical display. At step 233, placing a test sample in the sample chamber. At step 235, directing a first laser having a first wavelength of light through a first optical path to output the first laser from the dual magnification apparatus at a first magnification level. At step 237 directing the first laser at the first magnification level onto a first target area of the test sample. At step 239, applying an electrical stimulus to the test sample with an external stimulation device. At step 241, recording a first plurality of images of signal activity resulting from the first laser reflecting off of the first target area with the first wavelength detector. At step 243, directing a second laser having a second wavelength of light through a second optical path to output the second laser from the dual magnification apparatus at a second magnification level. At step 245, directing the second laser at the second magnification level onto a second target area on the test sample to activate at least one fault condition within the test sample. At step 247, recording a second plurality of images of signal activity resulting from the second laser activating at least one fault condition and reflecting off of the second target area with a second wavelength detector. At step 249, localizing the location of the at least one fault condition by adjusting the second target area while monitoring the first and second pluralities of images until at least one local maximum of signal activity disruptions is found.

Although the invention has been described in detail with reference to certain preferred embodiments, variations and modifications exist within the spirit and scope of the invention as described and defined in the following claims.

The invention claimed is:
1. A dual magnification apparatus comprising:
a first lens assembly comprising a first and second optical doublet and a first dichroic optical assembly, wherein the first dichroic optical assembly reflects a first wavelength of light and is transmissive to a second wavelength of light;
a second lens assembly comprising a third, fourth, fifth, sixth, and seventh optical doublet and a first, second, and third reflecting element, wherein the first and second reflecting elements reflect light at about a ninety degree angle, wherein the first reflecting element is adjustable;
a third lens assembly comprising an eighth, ninth, tenth, eleventh, and twelfth optical doublet and a fourth, fifth, and sixth reflecting element, wherein the first and second reflecting elements reflect light at about a ninety degree angle, wherein the fourth reflecting element is adjustable; and
a fourth lens assembly comprising a second dichroic optical assembly, wherein the second dichroic optical assembly reflects the second wavelength of light and is transmissive to the first wavelength of light;
wherein a first optical path passes through the first and second optical doublets, reflects off of the first dichroic optical assembly, passes through the third and fourth optical doublets, reflects off of the first and second reflecting elements, passes through the fifth, sixth, and seventh optical doublets, reflects off of the third reflecting element, and passes through the second dichroic optical assembly;
wherein a second optical path passes through the first and second optical doublets, passes through the first dichroic optical assembly, reflects off of the fourth reflecting element, passes through the eighth and ninth optical doublets, reflects off of the fifth and sixth reflecting elements, passes through the tenth, eleventh, and twelfth optical doublets, and reflects off of the second dichroic optical assembly;
wherein the first optical path is configured to magnify light to a first magnification level;
wherein the second optical path is configured to magnify light to a second magnification level, wherein the second magnification level is higher than the first magnification level;
wherein a first plurality of light comprising a first wavelength of light follows the first optical path such that a first portion of the first plurality of light enters an ocular lens of the first optical doublet and exits an objective section of the second dichroic optical assembly and a second portion of the first plurality of light enters the objective section of the second dichroic optical assembly and exits the ocular lens of the first optical doublet;
wherein a second plurality of light comprising a second wavelength of light follows the second optical path such that a first portion of the second plurality of light enters an ocular lens of the first optical doublet and exits an objective section of the second dichroic optical assembly and a second portion of the second plurality of light enters the objective section of the second dichroic optical assembly and exits the ocular lens of the first optical doublet;
wherein the first portion of the first plurality of light exiting the objective section of the second dichroic optical assembly is directed towards a first target area, wherein adjusting the first reflecting element shifts the first target area;
wherein the first portion of the second plurality of light exiting the objection section of the second dichroic optical assembly is directed towards a second target area, wherein the second target area is within the first target area, wherein adjusting the fourth reflecting element shifts the second target area.
2. The apparatus of claim 1, wherein the first and second pluralities of light are lasers.
3. A dual magnification system comprising:
a dual magnification apparatus comprising:
a first lens assembly comprising a first and second optical doublet and a first dichroic optical assembly, wherein the first dichroic optical assembly reflects a first wavelength of light and is transmissive to a second wavelength of light;
a second lens assembly comprising a third, fourth, fifth, sixth, and seventh optical doublet and a first, second, and third reflecting element, wherein the first and second reflecting elements reflect light at about a ninety degree angle, wherein the first reflecting element is adjustable;
a third lens assembly comprising an eighth, ninth, tenth, eleventh, and twelfth optical doublet and a fourth, fifth, and sixth reflecting element, wherein the first and second reflecting elements reflect light at about a ninety degree angle, wherein the fourth reflecting element is adjustable; and
a fourth lens assembly comprising a second dichroic optical assembly, wherein the second dichroic optical assembly reflects the second wavelength of light and is transmissive to the first wavelength of light;
wherein a first optical path passes through the first and second optical doublets, reflects off of the first dichroic optical assembly, passes through the third and fourth optical doublets, reflects off of the first and second reflecting elements, passes through the fifth, sixth, and seventh optical doublets, reflects off of the third reflecting element, and passes through the second dichroic optical assembly;
wherein a second optical path passes through the first and second optical doublets, passes through the first dichroic optical assembly, reflects off of the fourth reflecting element, passes through the eighth and ninth optical doublets, reflects off of the fifth and sixth reflecting elements, passes through the tenth, eleventh, and twelfth optical doublets, and reflects off of the second dichroic optical assembly;

wherein the first optical path is configured to magnify light to a first magnification level;

wherein the second optical path is configured to magnify light to a second magnification level, wherein the second magnification level is higher than the first magnification level;

wherein a first plurality of light comprising a first wavelength of light follows the first optical path such that a first portion of the first plurality of light enters an ocular lens of the first optical doublet and exits an objective section of the second dichroic optical assembly and a second portion of the first plurality of light enters the objective section of the second dichroic optical assembly and exits the ocular lens of the first optical doublet;

wherein a second plurality of light comprising a second wavelength of light follows the second optical path such that a first portion of the second plurality of light enters an ocular lens of the first optical doublet and exits an objective section of the second dichroic optical assembly and a second portion of the second plurality of light enters the objective section of the second dichroic optical assembly and exits the ocular lens of the first optical doublet;

wherein the first portion of the first plurality of light exiting the objective section of the second dichroic optical assembly is directed towards a first target area, wherein adjusting the first reflecting element shifts the first target area;

wherein the first portion of the second plurality of light exiting the objection section of the second dichroic optical assembly is directed towards a second target area, wherein the second target area is within the first target area, wherein adjusting the fourth reflecting element shifts the second target area;

a first and second light generator configured to generate the first and second pluralities of light, respectively;

a first and second light detector configured to detect the first and second wavelength of light, respectively, and generate a first and second plurality of electronic signals upon detecting the respective wavelengths of light;

a control computer configured to activate the first and second light generators, further configured to receive and record the first and second pluralities of electronic signals from the first and second light detectors, convert the first and second pluralities of electronic signals into a first and second plurality of graphical signals, and send the first and second pluralities of graphical signals to a graphical user interface; and the graphical user interface configured to convert the first and second pluralities of graphical signals into a first and a second display image of the first and second target areas, respectively;

wherein the second portions of the first and second pluralities of light are directed towards the first and second light detectors, respectively.

4. The system of claim 3, wherein the first and second light generators are a first and second laser generator, respectively, wherein the first and second pluralities of light are lasers.

5. The system of claim 3, further comprising an external stimulation device, wherein the external stimulation device is configured to apply a stimulus to a test sample, wherein the control computer is further configured to activate the external stimulation device.

6. The system of claim 5, wherein the stimulus is an electric current, wherein the external stimulation device is further configured to pass the electric current through the test sample.

7. The system of claim 5, wherein the stimulus is heat, wherein the external stimulation device is further configured to heat the test sample.

8. The system of claim 3, wherein the first and the second display images are displayed simultaneously.

9. The system of claim 8, wherein the second display image is displayed within the first display image.

10. A method of examining a test sample comprising:

placing a testing sample in a sample chamber;

directing a first plurality of light having a first wavelength of light through a first optical path to output the first plurality of light from a dual magnification apparatus at a first magnification level;

directing the first plurality of light at the first magnification level onto a first target area of the testing sample;

recording a first plurality of images resulting from the first plurality of light reflecting off of the first target area with a first wavelength detector;

directing a second plurality of light having a second wavelength of light through a second optical path to output the second plurality of light from the dual magnification apparatus at a second magnification level;

directing the second plurality of light at the second magnification level onto a second target area on the testing sample to elicit testing sample responses;

recording a second plurality of images resulting from the second plurality of light activating a sample response and reflecting off of the second target area with a second wavelength detector; and localizing the location of at least one condition of interest by adjusting and scanning the second target area while monitoring the first and second pluralities of images until at least one local maximum of testing sample responses is found.

11. The method of claim 10 further comprising:

displaying the first and second pluralities of images of signal activity on a graphical user interface.

12. A method of examining a test sample comprising:

providing a dual magnification system comprising:

a dual magnification apparatus comprising:

a first lens assembly comprising a first and second optical doublet and a first dichroic optical assembly, wherein the first dichroic optical assembly reflects a first wavelength of light and is transmissive to a second wavelength of light;

a second lens assembly comprising a third, fourth, fifth, sixth, and seventh optical doublet and a first, second, and third reflecting element, wherein the first and second reflecting elements reflect light at about a ninety degree angle, wherein the first reflecting element is adjustable;

a third lens assembly comprising an eighth, ninth, tenth, eleventh, and twelfth optical doublet and a fourth, fifth, and sixth reflecting element, wherein the first and second reflecting elements reflect light at about a ninety degree angle, wherein the fourth reflecting element is adjustable; and a fourth lens assembly comprising a second dichroic optical assembly, wherein the second dichroic optical assembly reflects the second wavelength of light and is transmissive to the first wavelength of light;

wherein a first optical path passes through the first and second optical doublets, reflects off of the first dichroic optical assembly, passes through the third and fourth optical doublets, reflects off of the first and second reflecting elements, passes through the fifth, sixth, and seventh optical doublets, reflects off of the third reflecting element, and passes through the second dichroic optical assembly;

wherein a second optical path passes through the first and second optical doublets, passes through the first dichroic optical assembly, reflects off of the fourth reflecting element, passes through the eighth and ninth optical doublets, reflects off of the fifth and sixth reflecting elements, passes through the tenth, eleventh, and twelfth optical doublets, and reflects off of the second dichroic optical assembly;

wherein the first optical path is configured to magnify light to a first magnification level;

wherein the second optical path is configured to magnify light to a second magnification level, wherein the second magnification level is higher than the first magnification level;

wherein a first plurality of light comprising a first wavelength of light follows the first optical path such that a first portion of the first plurality of light enters an ocular lens of the first optical doublet and exits an objective section of the second dichroic optical assembly and a second portion of the first plurality of light enters the objective section of the second dichroic optical assembly and exits the ocular lens of the first optical doublet;

wherein a second plurality of light comprising a second wavelength of light follows the second optical path such that a first portion of the second plurality of light enters an ocular lens of the first optical doublet and exits an objective section of the second dichroic optical assembly and a second portion of the second plurality of light enters the objective section of the second dichroic optical assembly and exits the ocular lens of the first optical doublet;

wherein the first portion of the first plurality of light exiting the objective section of the second dichroic optical assembly is directed towards a first target area, wherein adjusting the first reflecting element shifts the first target area;

wherein the first portion of the second plurality of light exiting the objection section of the second dichroic optical assembly is directed towards a second target area, wherein the second target area is within the first target area, wherein adjusting the fourth reflecting element shifts the second target area;

a first and second light generator configured to generate the first and second pluralities of light, respectively;

a first and second light detector configured to detect the first and second wavelength of light, respectively, and generate a first and second plurality of electronic signals upon detecting the respective wavelengths of light;

a control computer configured to activate the first and second light generators, further configured to receive and record the first and second pluralities of electronic signals from the first and second light detectors, convert the first and second pluralities of electronic signals into a first and second plurality of graphical signals, and send the first and second pluralities of graphical signals to a graphical user interface;

the graphical user interface configured to convert the first and second pluralities of graphical signals into a first and second display image of the first and second target areas, respectively; and an external stimulation device, wherein the external stimulation device is configured to apply a stimulus to a test sample, wherein the stimulus is an electric current, wherein the external stimulation device is further configured to pass the electric current through the test sample, wherein the external stimulation device is further configured to heat the test sample;

wherein the control computer is further configured to activate the external stimulation device;

wherein the second portions of the first and second pluralities of light are directed towards the first and second light detectors, respectively;

wherein the first and second light generators are a first and second laser generator, respectively, wherein the first and second pluralities of light are lasers;

wherein the first and the second display images are displayed simultaneously;

placing the test sample in a sample chamber, wherein the test sample comprises at least one integrated circuit and at least one biological cell;

directing the first plurality of light through the first optical path to output the first portion of the first plurality of light from the dual magnification apparatus at a first magnification level;

directing the first portion of the first plurality of light at the first magnification level onto the first target area, where the first target area is on the test sample;

applying an electrical stimulus to the test sample and heating the test sample with an external stimulation device;

recording a first plurality of images of signal activity resulting from the first plurality of light reflecting off of the first target area with the first wavelength detector;

directing the first portion of the second plurality of light through the second optical path to output the first portion of the second plurality of light from the dual magnification apparatus at a second magnification level;

directing the first portion of the second plurality of light at the second magnification level onto the second target area, wherein the second target area is on the test sample, to activate a condition of interest within the test sample;

recording a second plurality of images of signal activity resulting from the second plurality of light activating a fault condition and reflecting off of the second target area with a second wavelength detector; and localizing the location of the condition of interest by adjusting and scanning the second target area while monitoring the first and second pluralities of images until a local maximum of signal activity disruptions is found.

\* \* \* \* \*